United States Patent [19]

Hagihara

[11] 4,185,620
[45] Jan. 29, 1980

[54] OXYGEN MEASURING ELECTRODE ASSEMBLY

[76] Inventor: Bunji Hagihara, No. 8-17, Fujishirodai 2-chome, Suita-shi Osaka, Japan

[21] Appl. No.: 863,561

[22] Filed: Dec. 22, 1977

[30] Foreign Application Priority Data

Dec. 29, 1976 [JP] Japan .................................. 51/158119
Jun. 4, 1977 [JP] Japan ............................. 52/72996[U]

[51] Int. Cl.² ............................................. A61B 5/00
[52] U.S. Cl. .............................. 128/635; 204/195 B; 204/195 P
[58] Field of Search .................... 128/2 E, 2.1 E; 204/195 B, 195 P

[56] References Cited

U.S. PATENT DOCUMENTS

| | | | |
|---|---|---|---|
| 3,659,586 | 5/1972 | Johns et al. | 128/2 E |
| 3,795,239 | 3/1974 | Eberhard et al. | 128/2 E |
| 3,918,434 | 11/1975 | Lubbers et al. | 128/2 E X |
| 3,998,212 | 12/1976 | Reichenberger | 128/2 E |
| 4,005,700 | 2/1977 | Parker | 128/2 E |

OTHER PUBLICATIONS

Eberhard et al., "Continuous $PO_2$... Electrodes", Med & Biol. Eng., vol. 13, No. 3, pp. 436–442, May 1975.

Primary Examiner—Lee S. Cohen
Attorney, Agent, or Firm—Sughrue, Rothwell, Mion, Zinn and Macpeak

[57] ABSTRACT

An oxygen measuring electrode assembly for measuring an oxygen partial pressure in arterial blood in which a cylindrical anode and cathode are disposed coaxially in an insulator in such way that the former is placed in the latter. The end surfaces of said electrodes contact with the body surface via an electrode membrane which covers said electrodes with a suitable tension and holds an electrolyte solution layer on said electrode surfaces. Said electrode membrane is fixed on an annular end portion of a cylindrical holder of an electrically and thermally insulating material which surrounds said anode. A metal collar surrounding said holder bears a membrane-covering metal plate which has an opening through which an area of said electrode membrane is exposed to the body surface. Said membrane cover plate, which is connected to said collar and controlled to keep a desired temperature, heats said body surface and activates the blood capillary, that is arterializes the subcutaneous tissue. Thus the electrode can detect the arterial oxygen partial pressure.

9 Claims, 6 Drawing Figures

OXYGEN MEASURING ELECTRODE ASSEMBLY

BACKGROUND OF THE INVENTION

This invention relates to an oxygen measuring electrode assembly having an improved structure which is useful for transcutaneous measurement of oxygen partial pressure in an arterial blood oxygen. The transcutaneous arterial blood oxygen measuring electrode assembly (hereafter abbreviated as "transcutaneous arterial oxygen electrode") is a mechanism for detecting the oxygen partial pressure in the arterial blood of a person to be examined from his skin without directly examining the blood; therefore, the measurement is carried out non-invasively or without damage to any part of his body. Accordingly, this electrode assembly can play an important part in oxygen control of patients, especially newborn infants. Upon application of the electrode assembly of this type onto the skin of a person to be examined, the oxygen in the subcutaneous tissue is diffused through the skin and reaches the noble metal cathode through the electrode membrane, where the oxygen is reduced to provide electrolytic current. Therefore, the oxygen partial pressure value in the tissue can be detected from the value of this electrolytic current. In this case, if the skin in contact with the electrode through the electrode membrane is heated at a temperature as high as possible within a temperature in which the skin is not burned, the subcutaneous tissue adjacent to the electrode is locally arterialized. Accordingly, the oxygen partial pressure of the tissue measured by this method is close to the oxygen partial pressure of arterial blood oxygen. The extent of closeness of the above two values, the transcutaneously measured value and the true arterial value, depends largely on the extent of arterialization of the subcutaneous tissue and partly on the properties of the electrode membrane, shape and size of the cathode and other structures of the electrode assembly. There are two types of transcutaneous arterial oxygen electrode assemblies known in the art. However, each of the electrode assemblies has inherent defects in the electrode structure thereof, especially in the heating mechanism of the skin, size and shape of the cathode and suporting mechanism of the electrode membrane.

In a transcutaneous arterial oxygen electrode assembly of a known first prior art, the cathode is a thin platinum wire whose diameter is on the order of 0.015 mm, and this cathode together with a silver anode arranged in association therewith is covered with an oxygen permeable membrane (polytetrafluoroethylene film 12 microns in thickness) supporting an electrolyte solution on the surfaces of the both electrodes. This electrode membrane is fixed to the electrode supporting body with a rubber "O" ring. In the case of this electrode assembly, heating of the skin is carried out by the silver anode which is heated at a constant temperature (43° C. or 44° C.). In this heating mechanism, arterialization of the subcutaneous tissue is not sufficient, because the heated area of skin is limited by the small surface of the anode. In addition, the signal-to-noise ratio (S/N ratio) in this electrode assembly is very low because the electrodes are extremely small. Furthermore, as the planar membrane is fixed with the "O" ring, the membrane is liable to get crinkled at the fixed portion, therefore it is difficult for the electrode surfaces to be uniformly in contact with the membrane, and accordingly the electrode activity is unstable.

A transcutaneous arterial oxygen electrode assembly of a known second prior art is available on the market. In this electrode assembly, a relatively large (3 mm in diameter) gold cathode is employed, and the cathode and the anode are covered with an electrode membrane (polyester film 6 microns in thickness) which is fixed to the electrode holder with a sleeve. In this electrode assembly, heating of the skin is carried out by the gold cathode which is kept at a constant temperature (42° or 44° C.). In this heating mechanism, arterialization of subcutaneous tissue is not sufficient for the same reasons as described in the case of the first prior art. Although the cathode has a relatively large size (3 mm in diameter) in this second prior art, the size is still too small for the purpose of sufficient arterialization. The second significant drawback of this electrode assembly is that, as the cathode surface must be made large for heating and the amount of oxygen consumption thereof becomes large, the measured oxygen value is measured much less than the actual arterial value. In order to reduce the above drawback. Use of a membrane of very low oxygen permeability has been tried for the electrode membrane. However, this method results in a slow response of the electrode. Accompanying the large oxygen reduction on the cathode, the electrolyte is excessively consumed and the drift of the sensitivity of the electrode becomes considerably large. Furthermore, the peripheral portion of the cathode is different in reactivity from the central portion because these two portions are different from each other in distance from the anode and in supply of ionic components of the electrolyte.

Similarly as in the first prior art described above, the second prior art apparatus also has the drawback that the electrode activity is varied with the change of the contact pressure from the skin, and results in inaccurate measurement, because contact between the membrane and the electrode surface is unstable.

SUMMARY OF THE INVENTION

This invention is intended to eliminate the above-described drawbacks accompanying the conventional transcutaneous arterial oxygen electrode assemblies.

A principal object of the invention is to provide an oxygen electrode assembly having a system of heating the skin over a wide area so that the arterialization of the subcutaneous tissue is carried out satisfactorily even at a temperature causing no burning.

Another object of this invention is to provide a novel structure (ring) of the cathode whereby the reaction amount is suitably increased to improve the signal-to-noise (S/N) ratio while retaining the uniform reaction activity over the cathode surface.

Another object of the invention is to provide a novel means for loading the electrode membrane which provides uniform and stable contact with the cathode surface.

The foregoing objects and other objects of the present invention are accomplished by the following specific features:

(1) Unlike the conventional transcutaneous electrode assembly, in this invention the heating of skin is not carried out through the cathode or the anode. In the present electrode assembly, a metal section occupying a greater part of the electrode assembly is kept at a constant temperature and this part is thermally connected to a metal plate at the bottom of the electrode assembly and the skin is heated by this plate which has much larger area than that of the end surface of anode or cathode. In the prior arts, the skin is heated from the electrode through the electrolyte layer and the electrode membrane, but there is no such obstacle as the electrolyte layer or the electrode membrane in the present assembly. By these two advantages, large heating area and absence of interfering layer, heating of the skin is carried out more effectively and more accurately than in the prior arts.

(2) A tubular silver anode is arranged coaxially with an annular end of a platinum (or gold) cathode through insulating material, so that the cathode surface has a uniform reactivity with respect to the anode and the electrolyte. Since the end of the cathode is annular, the cathode has a large area as compared to a point electrode, and the electrode reactivity is sufficiently large for obtaining high S/N ratio.

(3) The end of the cathode and the part surrounding the cathode are protruded slightly from the level of the end of the anode. The electrode membrane is depressed with a cover plate having an opening through which a part of the electrode membrane covering the end of the cathode is exposed. In this way the membrane can contact stably with the cathode surface by the stretching force of the membrane. This cover plate is made of metal having a good heat conductivity, and is used, at the same time, for heating the skin as described before.

In each of the conventional electrode assemblies, no cover plate is employed for stretching the electrode membrane, accordingly the membrane is loosely stuck onto the electrode surface only be weak force. Therefore, it is difficult to maintain a stable layer of the electrolyte between the membrane and the electrode surface which determines the electrode sensitivity.

(4) The electrode membrane is bonded to the annular surface of the plastic section of the electrode holder which is positioned outside the electrolyte storing bath located outside the annular silver anode. Therefore, unlike the clamping mechanism with the "O" ring or the sleeve, the membrane is never crinkled, and therefore the uniform contact with the electrode is obtained. From the above reason, the sensitivity of the present assembly is much stabilized and the leakage of electrolyte is completely prevented. When the bonding of the membrane is carried out by a cohesive material (adhesive), the replacement of the electrode membrane can be readily achieved.

(5) The electrolyte storing groove is formed in the electrode holder around the end surface of the anode, and a sufficient amount of electrolyte is pooled here. The pressure in the electrolyte storing groove is balanced with the atmospheric pressure though a thin hole communicated to air. In this way, the contact condition between the electrode membrane and the electrode surface is kept constant irrespective of variation in temperature and atomospheric pressure.

COMPARISON OF THE PRESENT INVENTION TO THE PRIOR ARTS

The comparison of main features of the present transcutaneous electrode to the two prior arts is summarized in TABLE I. By these structural characteristics, the present electrode shows much better accuracy (higher ratio of measured $PO_2$ value per actual arterial $PO_2$), higher stability and other many stronger points than the two prior arts.

TABLE II

| Structures | Comparison of the present invention to the prior arts | | | |
|---|---|---|---|---|
| | The 1st prior art | The 2nd prior art | The present invention | |
| Cathode surface | point | disk | ring | (3 in FIG. 1) |
| Area of cathode surface | small | large | intermediate | |
| Heating of skin through | anode | cathode | body (collar) and plate | (8,7) |
| Heating area | *ring, small | disk, small | *ring, large | (7) |
| Membrane holding | by O-ring | by cup (sleeve) | bond to holder | (5') |
| Membrane pressure to electrode | loose | loose | stable | |
| Membrane protector | none | none | thin plate | (7) |

In each case of the 1st prior art or the present invention, heating area is ring shaped and has an opening in the center. However, by making the opening small, arterialization of the subcutaneous tissues is not affected by the presence of the opening in the heating area, since the blood stream spreads through the subcutaneous capillaries. It is very important for the same reason that, if the heating temperature is the same, heating area should be as large as possible for sufficient arterialization.

DESCRIPTION OF THE PREFERRED EMBODIMENTS

Figure 1:
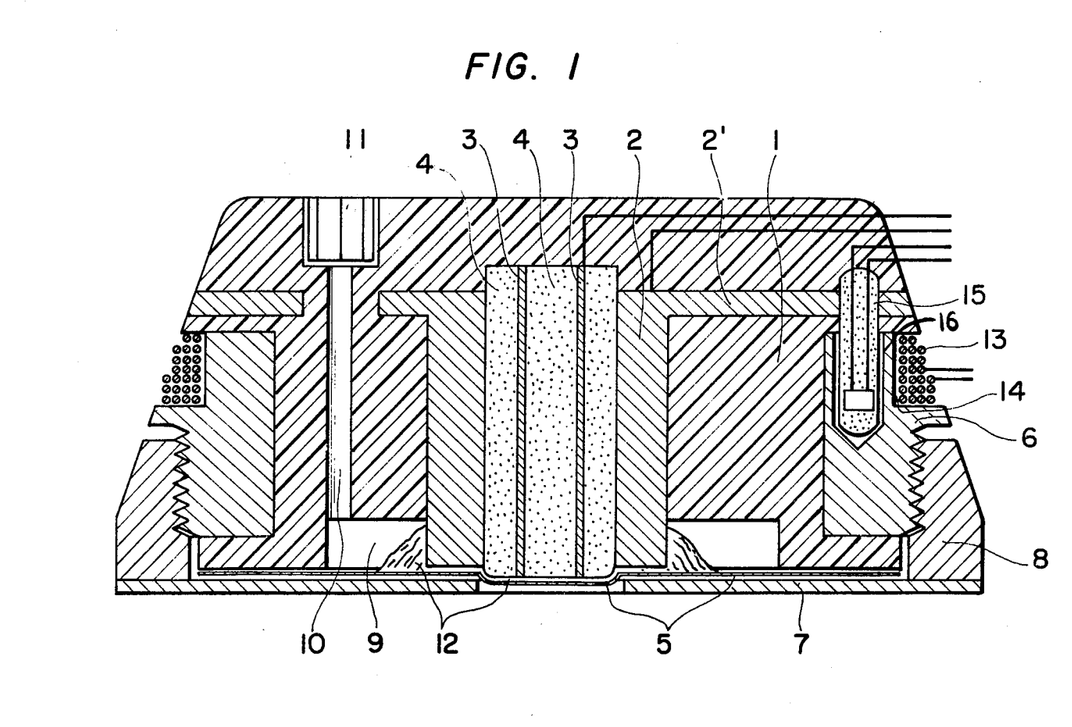
FIG. 1 is a sectional view showing the structure of one example of a measuring electrode assembly according to this invention.

FIG. 1 illustrates one embodiment of a transcutaneous oxygen measuring electrode assembly according to this invention. In FIG. 1, a reference numeral 1 designates an electrode holder of a suitable insulating material such as plastic and a cylindrical silver anode 2 which is buried in the holder 1 and whose lower end is exposed. An upper end of the anode 2 is provided with a flange 2' having a periphery exposed to an outer periphery of the holder 1. A cathode 3 is in the shape of a thin metal tube and spaced coaxially from the anode by a glass cylinder 4 fixed to the anode 2. A peripheral edge of an exposed end of the outer side of the cathode support cylinder 4 is rounded and the cathode support is arranged in such a manner that its end surface protrudes from the end surface of the anode 2 by a distance substantially equal to a radius of curvature of the rounded edge. On the other hand, the exposed end of the cathode 3 is in the same plane including the end of the cathode support cylinder 4.

An electrode membrane 5 is provided over the exposed ends of the electrodes 2 and 3 and the glass cylinder 4. The membrane 5 is an oxygen permeable film made of a hydrophobic polymer such as polyvinylidene chloride, polytetrafluoroethylene, or polypropylene. This membrane 5 is stuck on the peripheral part of lower end surface of the holder 1 with a suitable adhesive. In order to obtain a good contact of the membrane 5 to the cathode ends etc. while allowing the presence of an electrolyte layer 12 therebetween, the ends of the anode and the holder 1 are arranged in the same plane.

Further, the area of the membrane 5 the end of the anode 2 and the peripheral portion of the holder 1 are suitably compressed by a metal cover plate 7 having a central opening of similar size to that of the anode end to assure the intimate contact of the membrane 5 with these areas.

The cover plate 7 is supported by an outer metal collar 8 threaded to the collar 6. Therefore, the membrane 5 exposed only through the area of the opening of the cover plate 7 can be brought into contact with the surface of a body to be examined.

The end portion of the electrode holder 1 which is externally in contact with the end of the anode is suitably cut like a shoulder which is employed as an electrolyte pool 9 in the form of a circumferential groove. The excess part of an electrolyte 12 covering the surfaces of the anode 2 and the cathode 3 is maintained adhered to the groove, on the silver anode side. An air evacuating hole 10 is opened on the upper surface of the plastic section 4, extending through the holder 1 from a space outside the part of the groove where the electrolyte is maintained adhered. The opening of this hole 10 is plugged with a suitable gas permeating (porous) element 11. A number of small grooves (not shown) are provided in the end of the anode so as to stabilize the amount of electrolyte stored on the anode surface and to communicate the electrolyte balanced with the atmospheric pressure with the electrolyte layer on the end of the cathode.

A heater and a heat-sensitive element (thermister) are arranged at a suitable part of the electrode holder collar 6 which is made of a metal of high thermal conductivity. In the example shown in FIG. 1, the heater 13 is arranged in a circumferential (or peripheral) groove 14 provided in the holder collar 6, while the heat-sensitive element 15 is inserted into a hole 16 which is drilled in the holder collar 6.

Figure 2:
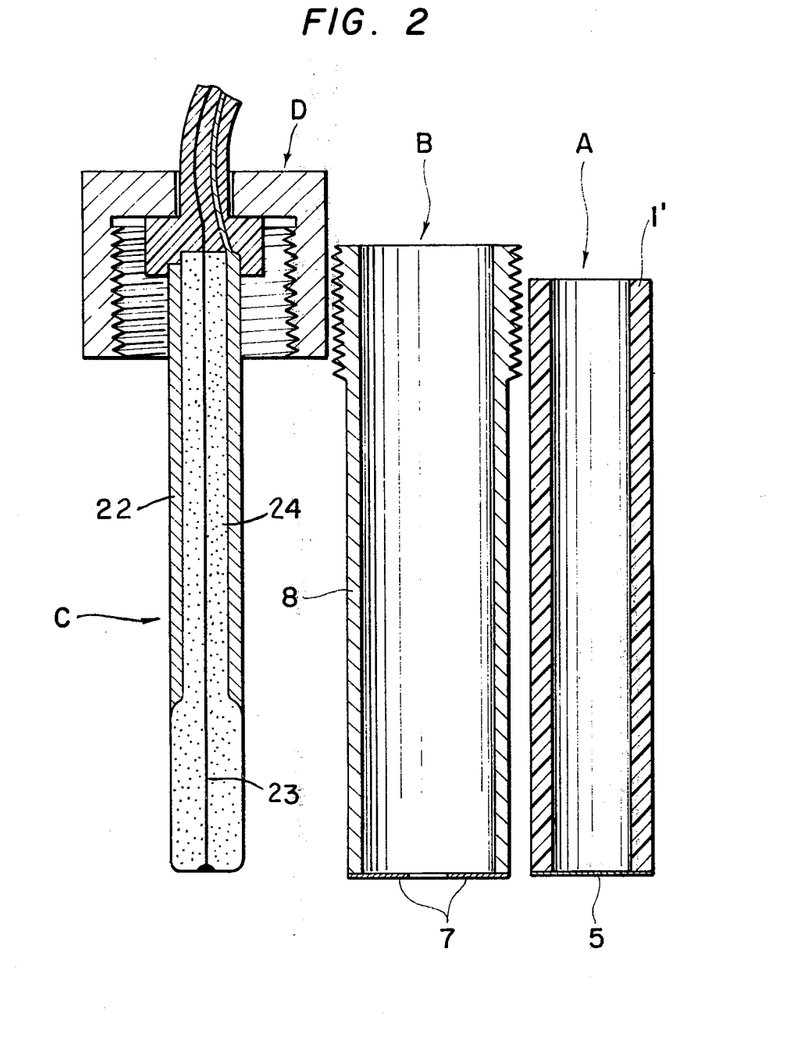
FIG. 2 is a sectional view of elementary parts of another embodiment of the present invention.
Figure 3:
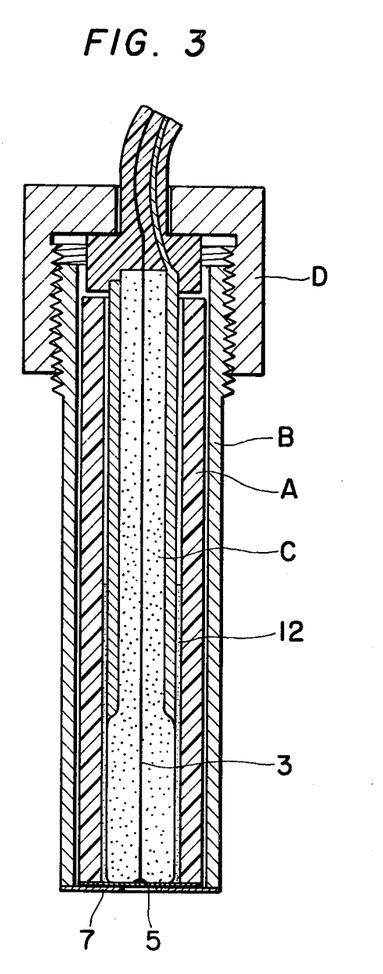
FIG. 3 is a sectional view showing an oxygen measuring electrode assembly composed of the parts shown in FIG. 2.

Another embodiment shown in FIGS. 2 and 3 has a structure which is easy in assembling and disassembling.

In FIG. 2, another oxygen measuring electrode assembly is shown in the disassembled state. The holder portion A is in the form of a circular tube, the lower end of the which is previously provided with an electrode membrane 5 which is of hydrophobic oxygen permeable material as in the previous embodiments. The material of the holder portion A is generally the same as that of the membrane 5 in order to facilitate the attachment of the membrane 5 to the lower end of the holder A by such as heat welding. However, different materials may be used for the holder portion.

The casing B is of a metal, e.g., stainless steel. However, other materials than metal may be used of the casing. At the lower end of the casing B, a resilient annular cover 7 is provided to compress the electrode membrane 5 when assembled. The upper outer end portion of the casing B if formed with a thread portion.

The electrode portion C comprises a cathode 23 of such as platinum or gold, an anode 22 of silver surrounding the cathode, an insulating member of such as glass for supporting the electrodes and a fastening member secured to the upper end of the electrode portion C, through which lead wires extend outwardly. The upper electrode cover portion D is in the form of having an inner thread.

In assembling operation, a small amount, e.g. several drops, of electrolyte is put on the membrane of the holder portion A, and then the holder portion A is inserted into the casing B. Thereafter the electrode portion C is inserted into the holder A and then the cover cap D is turned on the outer thread of the casing.

In FIG. 3, the oxygen electrode assembly is shown in the assembled state. The assembly comprises a holder portion A with a membrane, an electrode portion C disposed coaxially in the holder portion A, an outer casing B housing the holder portion A containing the electrode portion C therein and an upper cover portion D to be threaded on around the upper outer portion of casing B. The casing B corresponds to a combination of the outer collar and the membrane cover plate in FIG. 1.

Figure 4:
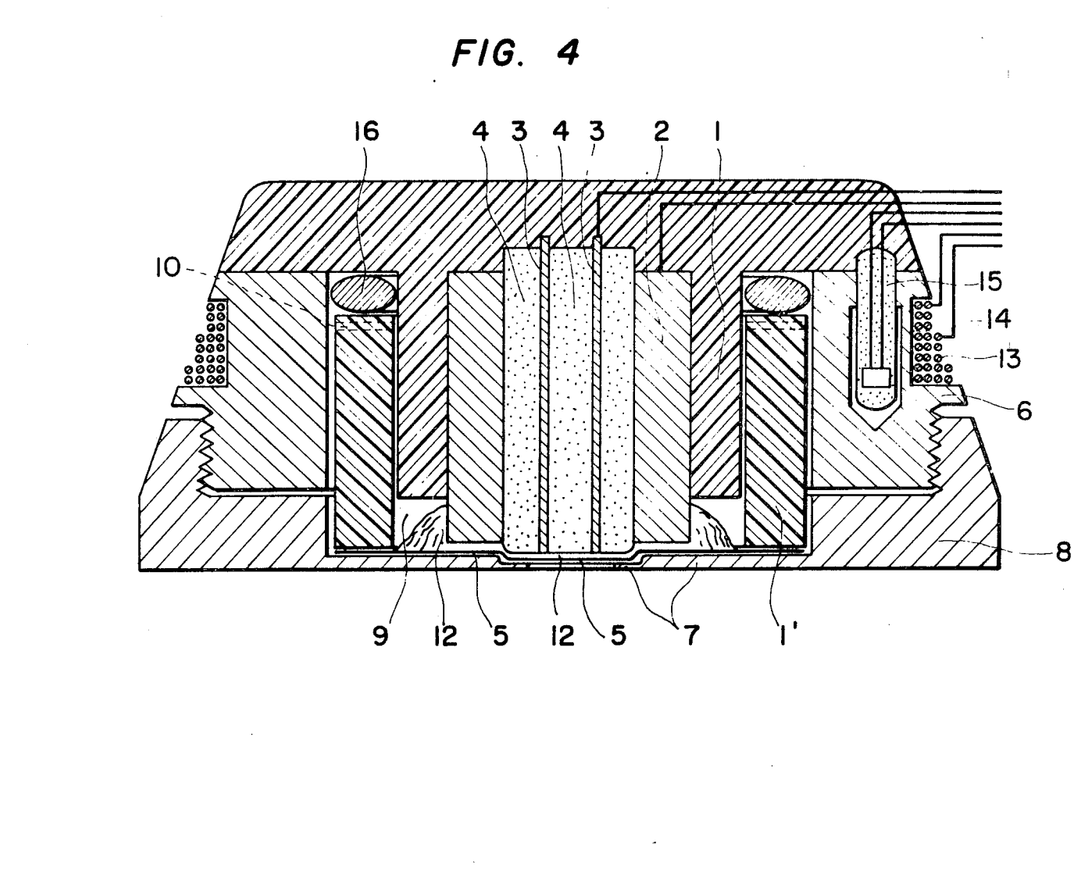
FIG. 4 is a sectional view of a modification of the embodiment in FIG. 1.

FIG. 4 illustrates a modified embodiment of an oxygen measuring electrode device according to this invention. This assembly is quite similar in structure to the assembly shown in FIG. 1, and only a part of the holder (1 in FIG. 1) is different. However, by this change, the loading of the electrode membrane becomes much easier and the contact between the membrane and the electrode is much stabilized. In FIG. 4, a reference numeral 1 designates a fixed part of electrode holder of a suitable insulating material such as plastics. A numeral 1' designates a detachable part of the holder which is in the form of a circular tube. The detachable tube 1' corresponding to the portion A in FIGS. 2 and 3, is provided at the lower end with an electrode membrane 5. A cylindrical silver anode 2 is buried in the fixed part 1 of the holder. A cathode 3 is in the shape of a thin metal tube and spaced coaxially from the anode 2 by a glass cylinder 4 fixed to the holder 1. A peripheral edge of an exposed lower end of the glass cylinder 4 supporting the cathode 3 is rounded and the cathode 3 is arranged in such a manner that the lower end of the glass cylinder protrudes downward from the end of the anode 2 by a distance substantially equal to a radius of curvature of the rounded edge. On the other hand, the exposed end of the cathode support cylinder 4 is in the plane including the cathode end.

An electrode membrane 5 which is made of hydrophobic oxygen permeable material is provided over the exposed ends of the electrodes 2 and 3 and the glass cylinder 4. The membrane 5 is made of an oxygen permeable hydrophobic material, and fixed on the lower end surface of the detachable part 1' of the holder portion with a suitable adhesive or by means of heat bonding. In order to obtain a good contact of the membrane 5 to the lower end surfaces of the anode while allowing the presence of an electrolyte layer inbetween, the lower end face of the anode 2 and that of the detachable part 1' are arranged in the same plane. The area of the membrane 5 covering lower end surface of the anode 2 is compressed by a metal cover plate 7 having a central opening of a size slightly larger than that of the lower end of the cathode support cylinder 4 to assume the intimate contact of the membrane 5 with these areas.

The cover plate 7 is supported by a collar 8 made with good heat conductive metal threaded to the collar 6 which is also made with a metal of good heat conductivity. By the presence of the cover plate 7, only the area of the membrane 5 exposed through the opening of the plate 7 can contact with the surface of a body to be examined.

The end portion of the fixed part 1 of the electrode holder, which is contact with the anode 2, suitably recedes from the end surface of the anode in order to form a circumferential space which serves as an electrolyte pool 9. An electrolyte 12 is maintained between the membrane 5 and the end surfaces of the electrodes, and its excess part is pooled in the above space 9.

A heater and a heat-sensitive element (thermister) are arranged at a suitable part of the electrode holder collar 6 which is made of a metal of good heat conductivity. The heater 13 is arranged in a circumferential (or peripheral) groove 14 provided in the holder collar 6, while the heat-sensitive element 15 is inserted into a hole which is drilled in the holder collar 6.

Since the electrode holder comprises the detachable part 1' with electrode membrane bonded thereto, it is easy to obtain a membrane of a desirable tension which has been preliminarily fabricated by a manufacturer under good quality control.

In the electrode assembly shown in FIG. 4, the flange portion 2' of the anode 2 shown in FIG. 1 is eliminated. There is no essential difference between the presence and the absence of this flange portion as a component of the oxygen electrode assembly for the performance of transcutaneous measurement of arterial oxygen partial pressure.

Two examples of the data obtained by the transcutaneous arterial oxygen electrode assembly shown in FIG. 1 will be described. The conditions of constructing the electrode assembly used in these experiments are listed below:

| | |
|---|---|
| Cathode | Material - gold |
| | Outside diameter of the surface - 2.0 mm |
| | Inside diameter of the surface - 1.5 mm |
| Anode | Material - silver |
| | Outside diameter of the surface - 5 mm |
| | Inside diameter of the surface - 3 mm |
| Electrolyte | Water - glycerol - KCl - buffer solution (pH 10) |
| Electrode membrane | Polyvinylidene chloride film, 12 μ in thickness |

Response Curve With Respect to Gas Exchange (Calibration Curve)

Figure 5:
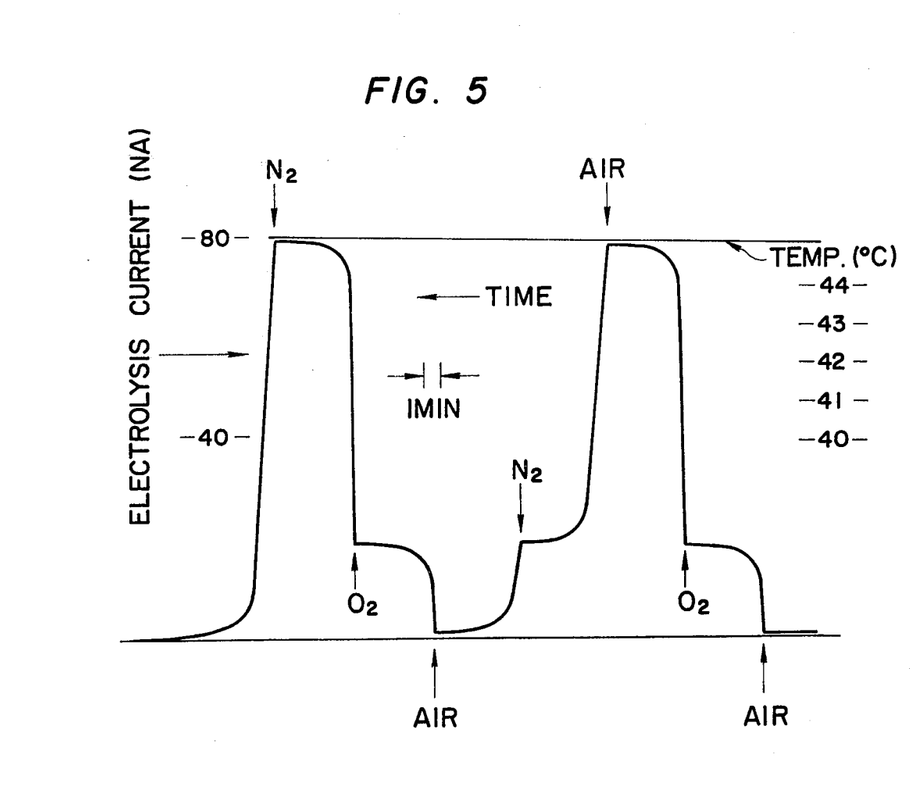
FIG. 5 is a graphical representation showing a change in the electrolysis current, with respect to gas exchange, of the transcutaneous oxygen electrode assembly according to the present invention.

The curve is as shown in FIG. 5. The above-described electrode assembly according to this invention was set in a calibration chamber (which is a gas exchange container approximately 5 ml in capacity having a small hole in the upper part, which is in contact with the electrode assembly). The electrolysis current of the electrode assembly was recorded while nitrogen gas, air and oxygen were supplied alternately to the chamber. The response characteristic of the electrode assembly, the linearity with respect to the oxygen partial pressure (concentration) and other properties of the assembly were examined from this curve. The results of this examination indicate the following characteristics; (1) The residual current is less than 0.2% with respect to the 1 atm. (760 mm Hg) $O_2$ valve; (2) The 80% response time is 30 seconds, and the 96% response time is 70 seconds (this means that the reaction is substantially in accordance with the curve of first degree); (3) The linearity of the measurement values with respect to the $O_2$ concentration is substantially proportional, judging from the comparison of currents for $N_2(O_2=0)$, air ($O_2=20.99\%$) and $O_2$.

Figure 6:
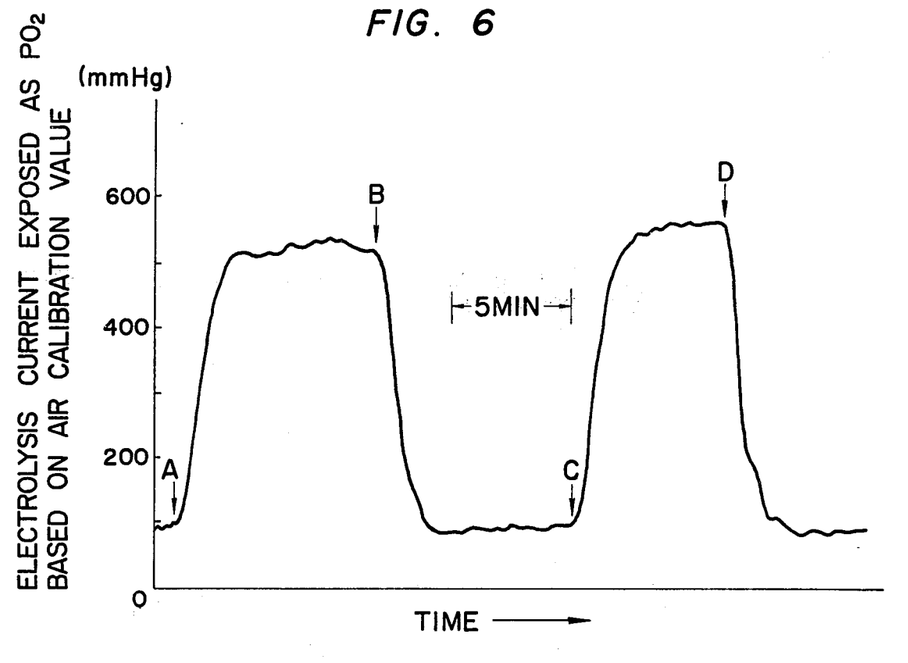
FIG. 6 is a graphical representation showing a time course of electrolysis current actually measured by a transcutaneous oxygen electrode assembly (44° C.) on the forearm skin of a person (♀, age 26).

In the experiment shown in FIG. 6, the temperatures of the electrode assembly (set to a temperature of 44° C.) were also recorded. This time course is shown in the figure as an essentially straight line parallel with the abscissa. It was known from this line that the variation of the temperature during the experiment was less than 0.02° C.

Transcutaneous Experimental Value

A person examined was a woman 26 years old. The electrode assembly according to this invention was fixedly secured to the skin of the inside of her wrist by using a double faced adhesive tape. The electrode assembly was maintained at a temperature 45.5°±0.02° C. While she was allowed to make an air breathing exercise and an oxygen breathing exercise alternately, and the electrolytic current values were recorded. The results are as indicated in FIG. 6. Arrows A, B, C and D in the figure indicate the starting time of weak oxygen-breathing, air breathing, strong oxygen-breathing, respectively. As is apparent from the graphical representation shown in FIG. 6, the transcutaneous measured oxygen partial pressure during the air breathing exercise is about 90 mm Hg which is close to the standard value of the arterial blood oxygen partial pressure of the ordinary adult. When the oxygen inhalation was performed moderately, the oxygen partial pressure was about 530. When the oxygen inhalation was performed heavily, the oxygen partial pressure was 570. These values are well coincident with those of the actual arterial blood oxygen levels in the above conditions. The responses at the start and the stop of the oxygen inhalation are somewhat slower than the actual variations in the artery; however, the responses are sufficiently rapid for actual clinical treatments.

Essentially the same (or somewhat better) results were obtained by the transcutaneous oxygen electrode assembly shown in FIG. 4, as in the above experiments carried out by the assembly shown in FIG. 1.

The use of the conventional transcutaneous arterial oxygen electrode assembly is limited in application to only infants. However, in the electrode assembly according to this invention, the area adapted to heat a skin is markedly increased, and various improvements have been made. Accordingly, with the electrode assembly according to the invention, arterialization is satisfactorily caused even for adults, and useful and accurate measurements can be carried out. This is a significant advantage of the invention.

If the above-described measurement data and the results of usage of the electrode assembly according to the invention are collectively considered and are compared with those of the electrode assembly available on the market, the invention has the following merits: As the configuration and area of the cathode of the electrode assembly according to the invention are made suitable, the uniformity in reaction on the electrode surface and the S/N ratio of the electrode assembly reaction are both improved. In addition, as the holding mechanism of the electrode membrane and those of the additional components thereof are also improved in various ways, the stability in measurement is remarkably improved. These merits contribute to the stable heating operation and to the sufficient heat transmission to a surface to be examined, and make it possible to perform the transcutaneous arterial blood oxygen measurement of an adult which has been difficult before, in association with the selection of the suitable film for the electrode assembly.

What is claimed is:

1. An oxygen measuring electrode assembly comprising an electrode portion having a tubular anode electrode and a tubular cathode electrode of a smaller diameter than the said anode electrode and disposed coaxially in said anode electrode, each of said anode and cathode having lower ends, an insulating support member disposed between said anode and cathode and supporting both the electrodes with respect to each other with their lower ends exposed thereby to form said electrode portion having a lower end comprising the lower ends of said anode and cathode, an annular holder portion made of electrically and thermally insulating material and having a lower end, said holder portion surrounding said anode electrode, an electrode membrane bonded to the lower end of said holder portion so as to cover the lower end of said electrode portion, electrolyte solution disposed between said lower end surfaces of said electrodes and said electrode membrane, a collar portion, of a heat conductive metal having a large thermal capacity, surrounding and supporting said holder portion, said collar portion having a lower end, a temperature control means provided in said collar portion for maintaining the temperature of said collar portion at a desired value and a membrane cover plate covering said membrane and thermally connected to the lower end of said collar portion, said membrane cover plate having an opening through which an area of said membrane corresponding to the area of the lower end of said electrode portion is exposed, said membrane cover plate being adapted to transmit heat from said collar portion to the skin of a body to be examined so that a transcutaneous measurement of arterial blood oxygen partial pressure can be made.

2. An oxygen measuring electrode assembly as claimed in claim 1, wherein said insulating support member is made of glass.

3. An oxygen measuring electrode assembly as claimed in claim 1, wherein said holder portion is provided with an annular shoulder portion at its lower end to form an electrolyte pool, and an air passage communicating said electrolyte pool with atmosphere.

4. An oxygen measuring electrode assembly as claimed in claim 1, wherein said electrode membrane is provided on said lower end surface of said electrodes to cover said end surfaces and is compressed by said membrane cover plate such that said membrane is stretched with a suitable tension.

5. An oxygen measuring electrode assembly as claimed in claim 1, wherein said electrode membrane is bonded onto said lower end surface of said holder portion by an adhesive.

6. An oxygen measuring electrode assembly as claimed in claim 1, wherein said holder portion and said electrolyte membrane are made of the same kind of organic material and said membrane is bonded onto said lower end of said holder portion by thermal adhesive.

7. An oxygen measuring electrode assembly as claimed in claim 1, wherein said holder portion is composed of a fixed part surrounding said anode electrode and a detachable part with the electrode membrane bonded thereto.

8. An oxygen measuring electrode assembly as claimed in claim 7, wherein said detachable part and said electrode membrane are bonded to each other by adhesive.

9. An oxygen measuring electrode assembly as claimed in claim 7, wherein said detachable part and said electrode membrane are made of the same kind of organic material and bonded to each other by thermal adhesive.

* * * * *